United States Patent
Gumery et al.

(10) Patent No.: US 8,465,438 B2
(45) Date of Patent: Jun. 18, 2013

(54) RESPIRATORY DIAGNOSTIC DEVICE

(75) Inventors: Pierre-Yves Gumery, Grenoble (FR); Laurent Heyer, Paris (FR)

(73) Assignees: Universite Joseph Fourier, Grenoble Cedex (FR); Assistance Publique, Paris Cedex (FR)

( * ) Notice: Subject to any disclaimer, the term of this patent is extended or adjusted under 35 U.S.C. 154(b) by 401 days.

(21) Appl. No.: 12/680,025

(22) PCT Filed: Sep. 23, 2008

(86) PCT No.: PCT/FR2008/051699
§ 371 (c)(1),
(2), (4) Date: May 11, 2010

(87) PCT Pub. No.: WO2009/050364
PCT Pub. Date: Apr. 23, 2009

(65) Prior Publication Data
US 2010/0256513 A1    Oct. 7, 2010

(30) Foreign Application Priority Data
Sep. 25, 2007 (FR) .................... 07 57834

(51) Int. Cl.
*A61B 5/04* (2006.01)
(52) U.S. Cl.
USPC ............................ 600/529; 600/534; 600/546
(58) Field of Classification Search
USPC ........................................ 600/529–543, 546
See application file for complete search history.

(56) References Cited

U.S. PATENT DOCUMENTS

| | | | | |
|---|---|---|---|---|
| 5,513,631 | A | * | 5/1996 | McWilliams ............ 128/204.23 |
| 5,820,560 | A | * | 10/1998 | Sinderby et al. ............... 600/546 |
| 2007/0276280 | A1 | * | 11/2007 | Blomberg et al. ............. 600/546 |

FOREIGN PATENT DOCUMENTS

WO        99/62580 A      12/1999

OTHER PUBLICATIONS

PM Surat R. McTier, SC Wilhoit: "Alae nasi electromyographic activity and timing in obstructive sleep apnea" J. Appl. Physiol, 1985, pp. 1252-1256, XP009099989.
A. Vila, P. Levy, F. Blanc-Jouvan, P.Y. Gumery, G. Quezel, P.D. Thuan, "Respiratory Muscle Fatigue Diagnosis and Automatic Analysis of EMG Signals", Electroencepahlography and Clinical Neutronphysiology, 1988, pp. 55-55, XP002479550.
L. Heyer, P.F. Baconnier, A. Eberhard, L. Biot, J.P. Viale, J.P. Perdrix, P.Y. Carry: "Non-invasive Detection of Respiratory Muscles Activity During Assisted Ventilation", Comptes Rendues Biologies, 2002, pp. 383-391, XP002479551.
American Thoracic Society (ATS) and the European Respiratory Society (ERS): "ATS/ERS Statement on Respiratory Muscle Testing", Am J Respir Crit Care Med, 2002, pp. 518-624, XP002479552, pp. 548-554, pp. 593-600, pp. 610-619.
International Search Report issued in PCT/FR2008/051699 on Oct. 14, 2009.

* cited by examiner

*Primary Examiner* — Patricia Mallari
*Assistant Examiner* — Tiffany Weston
(74) *Attorney, Agent, or Firm* — Vedder Price PC

(57) ABSTRACT

The invention relates to a device for analyzing a patient's respiratory status, including: means for determining electromyographic activity (EMG-AN) at the wings of the patient's nose and the start of nasal contractions; means for determining electromyographic activity (EMG-THO) at the patient's thorax and the start of thoracic inspiratory contractions; means for determining the rostro-caudal delay between the start of the nasal contractions and the start of the thoracic inspiratory contractions; means for comparing the delay to a threshold; and means for supplying an alarm signal when the delay is above said threshold.

7 Claims, 2 Drawing Sheets

RESPIRATORY DIAGNOSTIC DEVICE

FIELD OF THE INVENTION

The present invention relates to a device for analyzing a patient's respiratory state, and especially to the application of such a device to the control of a respiratory ventilator.

DISCUSSION OF PRIOR ART

In various clinical cases, for example, for a patient in a coma, the patient must be placed under respiratory assistance. He is then connected to a device called a breathing machine or a respiratory ventilator.

One of the problems posed by respiratory assistance is how to determine the time at which the patient can be disconnected so that natural breathing takes over from the assistance. Currently, respiratory ventilators are not equipped with detectors enabling to determine when a separation can occur in safe conditions, and this determination is performed empirically, with the possible assistance of electronic expert systems.

SUMMARY OF THE INVENTION

Thus, a specific object of the present is to provide a device for controlling a respiratory ventilator, which enables to indicate when this ventilator can be safely disconnected.

The present invention more specifically aims at a device for analyzing a patient's respiratory state, for example enabling to detect sleep-related respiratory disorders (obstructive and central sleep apneas, upper airway resistance syndrome), and to control the delivery of drugs during an anesthesia, and more generally to detect respiratory failures.

To achieve these objects, the present invention provides a device for analyzing a patient's respiratory state, comprising means for determining the electromyographic activity at the level of the alae of a patient's nose and the beginning of nasal contractions; means for determining the electromyographic activity at the level of the patient's thorax and the beginning of thoracic inspiratory contractions; means for determining the rostro-caudal delay between the beginnings of the nasal contractions and of the thoracic inspiratory contractions; means for comparing said delay with a threshold; and means for providing an alarm signal when said delay is greater than said threshold.

The present invention also provides a device for controlling a respiratory ventilator comprising means for determining the electromyographic activity at the level of the alae of a patient's nose and of the beginning of nasal contractions; means for determining the electromyographic activity at the level of the patient's thorax and the beginning of thoracic inspiratory contractions; means for determining the rostro-caudal delay between the beginnings of the nasal contractions and of the thoracic inspiratory contractions; means for comparing said delay with a threshold; and means for generating a signal authorizing the ventilator to be stopped when said delay is smaller than said threshold.

According to an embodiment of the present invention, the electromyographic activity determination means comprise skin electrodes.

According to an embodiment of the present invention, an analog-to-digital converter receives the signals provided by said electrodes after a preprocessing, the digital signals being submitted to various filtering and shaping means before the comparison operations.

According to an embodiment of the present invention, the digital filtering comprises an adaptive heart signal filtering using an ECG signal sensed by other skin electrodes and a filtering at the mains frequency.

According to an embodiment of the present invention, the preprocessing is performed by amplification and filtering means.

According to an embodiment of the present invention, means for determining the sliding average of the rostro-caudal delay over several respiratory phases is provided.

According to an embodiment of the present invention, said threshold is settable between 200 and 1,000 ms.

BRIEF DESCRIPTION OF THE DRAWINGS

The foregoing objects, features, and advantages of the present invention, as well as others, will be discussed in detail in the following non-limiting description of specific embodiments in connection with the accompanying drawings, among which.

DETAILED DESCRIPTION

The present invention provides a device for comparatively analyzing a patient's electromyogram measured at the level of his or her nasal alae and at the level of his thorax and for processing the comparison signal to provide alert, safety range, or diagnostic signals.

Figure 1:
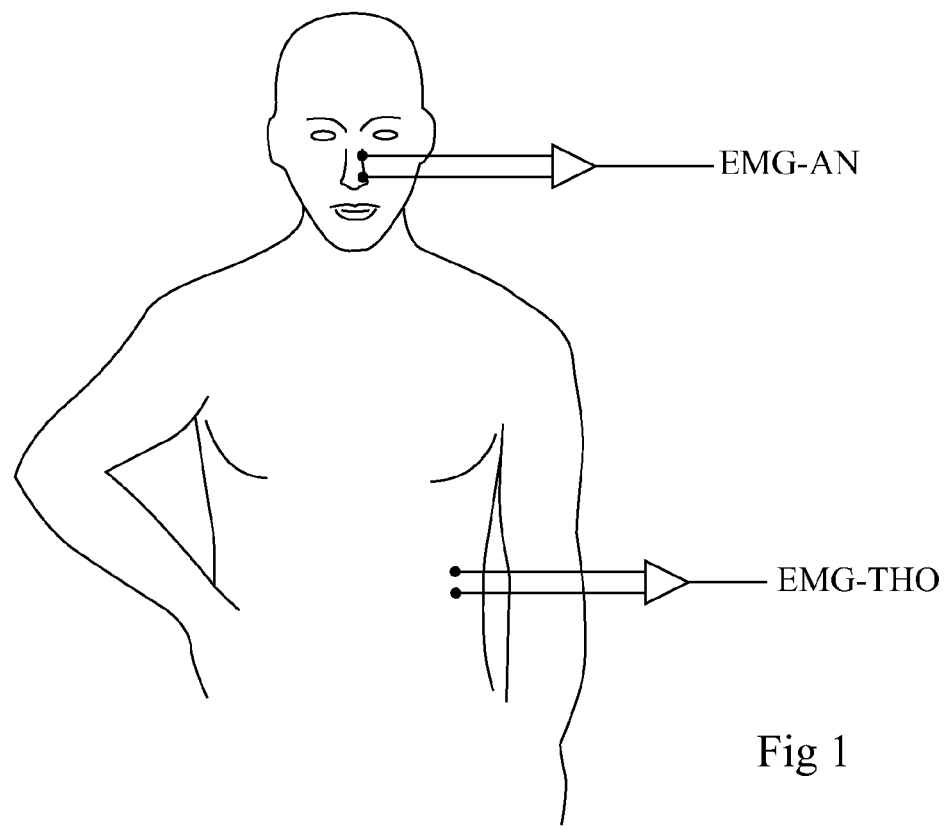
FIG. 1 schematically illustrates the positioning of electromyogram sensors according to an embodiment of the present invention.

In FIG. 1, the electromyogram signal at the level of the alae of the nose is called EMG-AN, and the electromyogram signal at the thorax level is called EMG-THO. The electromyogram signal at the thorax level is measured, for example, for the parietal diaphragmatic muscle between the seventh and eighth ribs. It should be understood that the electromyogram signals related to the low portion of the respiratory system may in certain cases of paralysis, be measured at other levels. The measured electromyograms are indicative of the activation of the muscles of the alae of the nose and of the inspiratory thoracic muscles when a patient is breathing. According to an aspect of the present invention, the electromyograms are non-invasively measured by skin electrodes.

Figure 2:
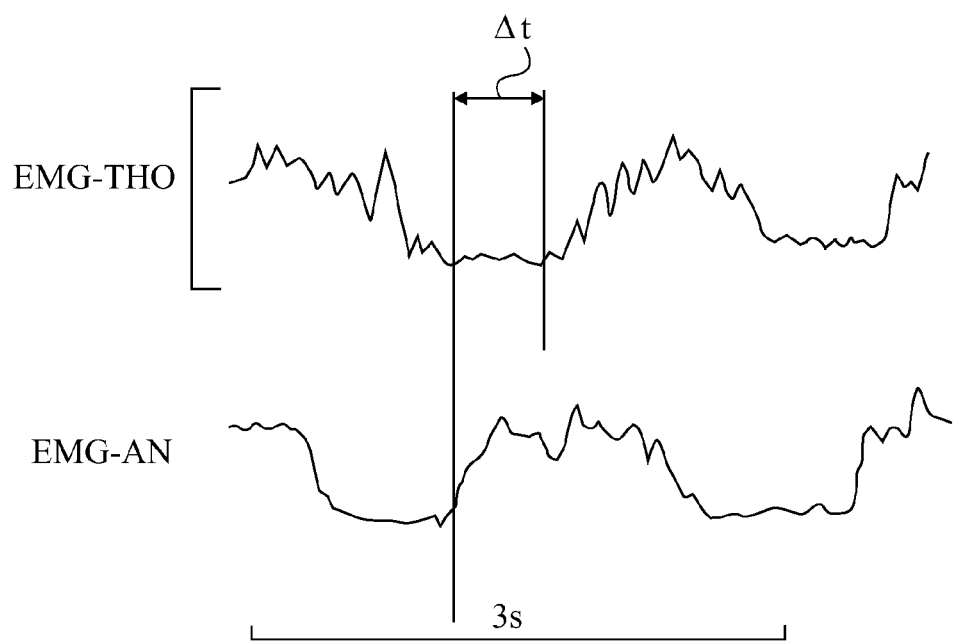
FIG. 2 shows electromyograms respectively measured at the level of a patient's alae of the nose and at the level of his thorax.

As illustrated by the curves of FIG. 2, for a normal patient, signal EMG-AN exhibits a growth phase which corresponds to a muscular contraction phase which precedes the phase of contraction of the inspiratory thoracic muscles by a period $\Delta t$. $\Delta t$ is currently called a rostro-caudal delay since it corresponds to the offset between the activation of the upper (or front) airways and the activation of the thoracic (or rear) inspiratory muscles.

The present invention provides to measure this delay $\Delta t$ and to give an indication according to this delay. More specifically, a device according to the present invention will provide a measurement of this delay and will compare it with a threshold to indicate that a patient is in a proper state. The value by which this threshold varies is determined according to the explored thoracic muscles. For example, the delay is greater if the detection is performed at the level of the parietal diaphragm rather than at that of the inspiratory intercostal muscles. For example, if the patient is under a respiratory ventilator, it will be indicated that this ventilator may be disconnected when the delay becomes shorter than a duration on the order of 500 ms. Indeed, an average breathing period is on the order of 5 seconds and it is considered that a patient is in a satisfactory state when this rostro-caudal delay approximately ranges from 0.2 to 0.3 second. Generally, the signal indicating that the rostro-caudal delay is or becomes lower than a threshold or, conversely, becomes greater than this threshold, may be used to provide a diagnostic signal. For example, in the context of anesthesia operations, it will be ascertained for the rostro-caudal delay not to become greater than a determined threshold.

Thus, the present invention provides a device enabling to measure the EMG-AN and EMG-THO electromyograms, to submit them to a processing to remove various parasitic signals, to clearly measure the delay between the time at which these signals start growing, and to compare this delay with a threshold to give an indication of the patient's state when the signal is smaller than the threshold. In an application to a breathing machine, the comparison signal, when it corresponds to an authorization to disconnect a breathing machine, may for example take the form of a blinking lamp on the ventilatory device, of a bell, or of a signal remotely provided on a control display.

Of course, preferably, the device may also comprise means for calculating the average of the delay over several respiratory cycles, to provide a sliding average. The device will then comprise means for determining whether this sliding average remains greater than a threshold for a determined time period, for example, a period approximately ranging from a few minutes to one hour according to the type of searched diagnostic.

Figure 3:
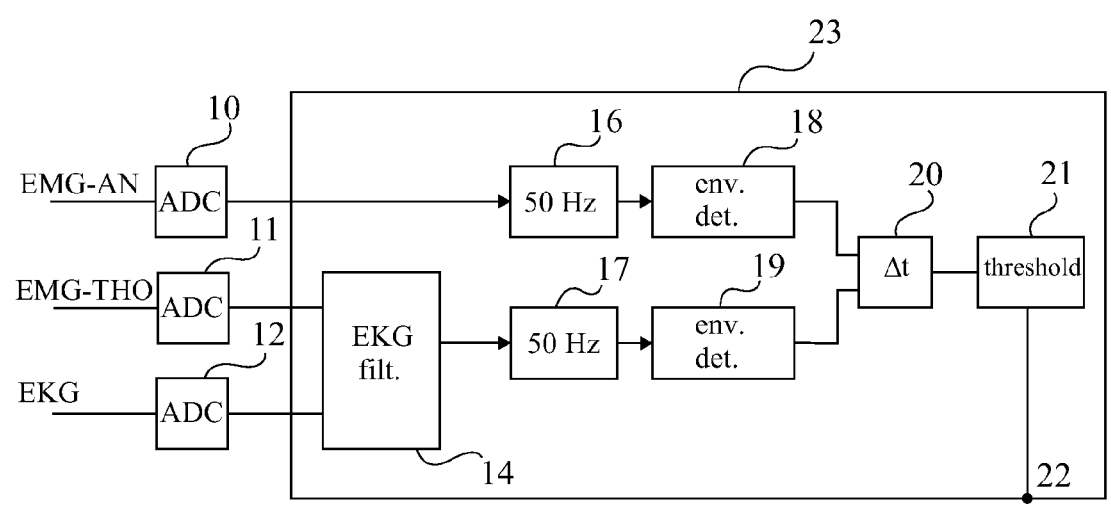
FIG. 3 shows an example of a device for processing electromyogram signals according to an embodiment of the present invention.

FIG. 3 shows an embodiment of a device 23 according to the present invention. Signals EMG-AN and EMG-THO, as well as an electrocardiogram EKG, are provided to analog-to-digital converters (ADC) 10, 11, and 12. Signals EMG-AN, EMG-THO, and EKG will preferably have been preprocessed, that is, for example, amplified and pre-filtered before the analog-to-digital conversion.

Then, signals EMG-THO and EKG are provided to a first filter 14 which removes the signals due to heartbeats from the electromyogram signals of the diaphragm. A similar filtering may be performed on the electromyogram signals of the alae of the nose, although this has not been shown. Then, the signals are provided to filters removing the mains frequency (currently, 50 hertz) 16 and 17. After this, devices 18 and 19 enable to provide the envelopes of digitized signals EMG-AN and EMG-THO. The outputs of envelope detectors 18 and 19 are provided to means 20 for calculating delay Δt between the beginning of the rise of the electromyogram signals of the alae of the nose and of the diaphragm. Delay Δt is provided to a device 21 for comparing value Δt with a threshold. Various devices for determining a sliding average and of comparison with a threshold for a given time period, may also be provided as indicated previously, an output enable signal 22 being provided only when given additional duration conditions are fulfilled.

Elements 14 to 21 have been previously described as hardware elements. In fact, in practice, all the functions performed by these various elements may advantageously be performed within a digital processor, for example, a microcomputer, receiving digitized signals EMG-AN, EMG-THO, and EKG and providing enable signal 22.

Although this has not been shown, comparison device 21 with a threshold will preferably be a comparison device with a settable threshold, adjustable by the nursing or medical staff according to the measurement which is desired to be performed.

The invention claimed is:

1. A device for analyzing a patient's respiratory state, comprising:
    a first analog-to-digital converter to convert a signal representative of electromyographic activity (EMG-AN) at a level of alae of a patient's nose and a beginning of nasal contractions to provide a first digitized signal;
    a second analog-to-digital converter to convert a signal representative of electromyographic activity (EMG-THO) at a level of the patient's thorax and a beginning of thoracic inspiratory contractions to provide a second digitized signal; and
    a processor, operatively connected to the first and second analog-to-digital converters, operative to:
    determine rostro-caudal delay between the beginnings of the nasal contractions of the first digitized signal and of the thoracic inspiratory contractions of the second digitized signal;
    compare said delay with a threshold; and
    generate an alarm signal when said delay is greater than said threshold.

2. A device for controlling a respiratory ventilator comprising:
    a first analog-to-digital converter to convert a signal representative of electromyographic activity (EMG-AN) at a level of alae of a patient's nose and a beginning of nasal contractions to provide a first digitized signal;
    a second analog-to-digital converter to convert a signal representative of determining electromyographic activity (EMG-THO) at a level of the patient's thorax and a beginning of thoracic inspiratory contractions to provide a second digitized signal; and
    a processor, operatively connected to the first and second analog-to-digital converters, operative to:
    determine rostro-caudal delay between the beginnings of the nasal contractions of the first digitized signal and of the thoracic inspiratory contractions of the second digitized signal;
    compare said delay with a threshold; and
    provide a signal authorizing the ventilator to be stopped when said delay is smaller than said threshold.

3. The device of claim 1 or 2, further comprising skin electrodes operatively connected to the first and second analog-to-digital converters.

4. The device of claim 3, wherein the first and second analog-to-digital converters receive the signals provided by said electrodes after preprocessing, the first and second digitized signals being filtered and shaped before the comparison of said delay with said threshold by the processor.

5. The device of claim 1 or 2, wherein the processor is further operative to provide adaptive heart signal filtering of at least one of the first and second digitized signals using an EKG signal sensed by other skin electrodes and to provide a filtering of the first and second digitized signals at the mains frequency.

6. The device of claim 4, wherein the preprocessing comprises amplification and pre-filtering.

7. The device of claim 1 or 2, wherein said threshold is settable between 200 and 1,000 ms.

* * * * *